US005403506A

United States Patent [19]

Jones

[11] Patent Number: 5,403,506
[45] Date of Patent: Apr. 4, 1995

[54] DEODORANT DETERGENT COMPOSITION

[75] Inventor: Keith A. Jones, Hopewell, N.J.

[73] Assignee: Church & Dwight Co., Inc., Princeton, N.J.

[21] Appl. No.: 129,427

[22] Filed: Sep. 30, 1993

[51] Int. Cl.$^6$ .......................... C11D 9/00; C11D 9/18
[52] U.S. Cl. .............................. 252/108; 252/174.14; 252/116; 252/128; 252/131
[58] Field of Search ................... 252/108, 174.14, 116, 252/128, 131

[56] References Cited

U.S. PATENT DOCUMENTS

| | | | |
|---|---|---|---|
| 3,284,363 | 11/1966 | Bright | 252/107 |
| 4,322,308 | 3/1982 | Hooper et al. | 252/106 |
| 4,587,029 | 5/1986 | Brooks | 252/91 |
| 4,847,071 | 7/1989 | Bissett et al. | 252/106 |
| 4,933,101 | 6/1990 | Cilley et al. | 252/99 |
| 5,000,870 | 3/1991 | Shimizu | 252/183.11 |

*Primary Examiner*—Linda Skaling
*Assistant Examiner*—Patricia L. Hailey
*Attorney, Agent, or Firm*—Charles B. Barris

[57] ABSTRACT

The disclosure describes deodorant detergent compositions comprising a surfactant, e.g., a soap or synthetic detergent, and as a deodorizing component, a minor amount of zinc oxide having an average particle size no greater than about 10 microns. To enhance its deodorizing effect, the composition optionally may contain a minor amount of sodium bicarbonate (SBC).

16 Claims, No Drawings

DEODORANT DETERGENT COMPOSITION

BACKGROUND OF THE INVENTION

1. Field of the Invention

The invention relates to a novel deodorant detergent composition.

2. Information Disclosure Statement Including Description of Related Art

The following information is being disclosed under the provisions of 37 CFR 1.56, 1.97 and 1.98.

Perspiration produced directly by the sweat glands of the body are generally odorless or have an innocuous odor. However, unpleasant body odors are often caused by the breakdown of the components of such perspiration by bacteria to produce foul-smelling substances such as butyric acid. Thus, deodorant detergent compositions, e.g., soaps, have been developed containing any of various additives known to act as bactericides or bacteriostats in order to keep the bacteria population on the skin low and hence minimize the breakdown of the perspiration components. It has been found, however, that the most widely used of these additives have certain disadvantages. For example, hexachorophene which was extensively used as a deodorizing additive for several years, has been shown to have a degree of neurotoxicity causing the U.S. Food and Drug Administration to prohibit its use unless prescribed by a physician. Triclocarban (3,4,4'-trichlorocarbanilide), which is presently used in many deodorant soaps, has been found to be a skin irritant in some instances. Thus, any deodorant detergent composition which does not have these disadvantages would be highly desirable.

U.S. Pat. No. 3,284,363, issued Nov. 8, 1966 to Bright, discloses germicidal soaps containing a combination of 3,4,5'-tribromsalicylanilide and 3,4,4'-trichlorocarbanilide (triclocarban) as germicides.

U.S. Pat. No. 4,587,029, issued May 6, 1986 to Brooks, discloses an intermediate product for use in producing a detergent bar, comprising a sodium salt of a fatty alcohol sulfuric acid or ethoxylated fatty alcohol sulfuric acid and sodium bicarbonate.

SUMMARY OF THE INVENTION

In accordance with the invention, a deodorant detergent composition is provided containing a surfactant, e.g., a soap or synthetic detergent, and as a deodorizing component, a minor amount, e.g., no higher than about 5 wt. %, of zinc oxide having an average particle size no greater than about 10 microns. Preferably, the composition also contains a minor amount, e.g., no higher than about 15 wt. %, of sodium bicarbonate (SBC). The composition is particularly useful as a personal toilet soap or detergent composition.

DETAILED DESCRIPTION OF THE INVENTION

The detergent compositions of this invention are solid or liquid and comprise a surface active or surfactant component, e.g., a soap or synthetic detergent, which contains a relatively polar hydrophilic group and a relatively non-polar hydrophobic group. The soaps are salts of relatively long chain fatty acids having the formula R—COO⁻X⁺, where R is often an unbranched saturated or unsaturated aliphatic group but may contain branches or even ring groups. Thus, the carboxylate (—COO⁻) groups constitute the hydrophilic groups of the soap molecule while the long carbon chain R groups constitute the hydrophobic groups. In order for the soap to have adequate solubility in water, the cation of the soap, X⁺, is usually an alkali metal, e.g., sodium or potassium, or, more rarely, an ammonium or substituted ammonium group.

Typical soaps contemplated under this invention are the water-soluble alkali metal, e.g., potassium and sodium, soaps of the saturated and unsaturated higher fatty acids having from about eight to about twenty-six carbon atoms, such as capric, caprylic, lauric, myristic, palmitic, stearic, oleic, linoleic, linolenic, arachidic, behenic, margaric, tridechoic, and cerotic acids and the mixtures of such acids naturally occurring in fats, oils, waxes and rosins, such as the soaps of coconut oil fatty acids, tallow fatty acids, pig fat, fish oil fatty acids, beeswax, palm oil fatty acids, sesame oil fatty acids, peanut oil fatty acids, olive oil fatty acids, palm kernel oil fatty acids, cottonseed oil fatty acids, soybean oil fatty acids, corn oil fatty acids, babassu oil fatty acids, rosin acids, abietic acid and greases.

Solid soaps generally comprise a predominantly sodium salt of longer chain and/or more saturated carboxylic acids present in a composition containing a relatively small amount of water. In contrast, the surfactant of a liquid soap often contains a substantial proportion of potassium and/or ammonium cations in place of or in addition to sodium ions. Moreover such liquid soap surfactant is usually a salt of a shorter chain and/or more unsaturated carboxylic acid, and is mixed with a larger percentage of water.

The synthetic detergents contemplated as surfactants under this invention are compounds other than soap whose detersive properties, like soap, are due to the presence of a hydrophilic and a hydrophobic group in the molecule. However, unlike soaps, synthetic detergents are not salts of carboxylic acids derived from fats and oils. Rather, the hydrophilic portion of the surfactant of a synthetic detergent is generally derived from a compound containing a relatively long carbon chain, e.g., a hydrocarbon obtained from petroleum refining and/or olefin polymerization or a long chain fatty acid, while the hydrophilic portion is the result of chemical modification of such compound to introduce the desired polar group, e.g., a hydroxyl, sulfate or sulfonate group.

The synthetic detergent compositions of this invention generally contain at least one anionic or nonionic surfactant or a mixture of the two types of surfactant.

The contemplated water soluble anionic detergent surfactants are the alkali metal (such as sodium and potassium) salts of the higher linear alkyl benzene sulfonates and the alkali metal salts of sulfated ethoxylated and unethoxylated fatty alcohols, and ethoxylated alkyl phenols. The particular salt will be suitably selected depending upon the particular formulation and the proportions therein.

The sodium alkybenzenesulfonate surfactant (LAS) most preferably used in the composition of the present invention has a straight chain alkyl radical of average length of about 11 to 13 carbon atoms.

Specific sulfated surfactants which can be used in the compositions of the present invention include sulfated ethoxylated and unethoxylated fatty alcohols, preferably linear primary or secondary monohydric alcohols with $C_{10}$–$C_{18}$, preferably $C_{12}$–$C_{16}$, alkyl groups and, if ethoxylated, on average about 1–15, preferably 3–12 moles of ethylene oxide (EO) per mole of alcohol, and sulfated ethoxylated alkylphenols with $C_8$–$C_{16}$ alkyl groups, preferably $C_8$–$C_9$ alkyl groups, and on average from 4–12 moles of EO per mole of alkyl phenol.

The preferred class of sulfated ethoxylated surfactants are the sulfated ethoxylated linear alcohols, such as the $C_{12}$–$C_{16}$ alcohols ethoxylated with an average of from about 1 to about 12 moles of ethylene oxide. A most preferred sulfated ethoxylated detergent is made by sulfating a $C_{12}$–$C_{15}$ alcohol ethoxylated with 3 moles of ethylene oxide.

Specific nonionic surfactants which can be used in the compositions of the present invention include ethoxylated fatty alcohols, preferably linear primary or secondary monohydric alcohols with $C_{10}$–$C_{18}$, preferably $C_{12}$–$C_{16}$, alkyl groups and on average about 1–15, preferably 3–12 moles of ethylene oxide (EO) per mole of alcohol, and ethoxylated alkylphenols with $C_8$–$C_{16}$ alkyl groups, preferably $C_8$–$C_9$ alkyl groups, and on average about 4–12 moles of EO per mole of alkyl phenol.

The preferred class of nonionic surfactants compounds are the ethoxylated linear alcohols, such as the $C_{12}$–$C_{16}$ alcohols ethoxylated with an average of from about 1 to about 12 moles of ethylene oxide. A most preferred nonionic detergent is a $C_{12}$–$C_{15}$ alcohol ethoxylated with 3 moles of ethylene oxide.

Mixtures of the foregoing synthetic detergent type of surfactants, e.g., of anionic and nonionic, or of different specific anionic or nonionic surfactants, may be used to modify the detergency, lather characteristics, and other properties of the composition. For example, a mixture of different fatty alcohols of 12 to 15 carbon atoms may be ethoxylated, directly sulfated, or sulfated after ethoxylation, a fatty alcohol may be partially ethoxylated and sulfated, or an ethoxylated fatty acid may be partially sulfated to yield a mixture of anionic and nonionic surfactants or different specific anionic or nonionic surfactants.

The zinc oxide utilized in the detergent compositions of this invention has an average primary (unagglomerated) particle size no higher than about 10 microns. Preferably, the primary particle size in the range of about 0.01 to 5 microns and most preferably about 0.01 to 0.1 microns. The specific surface area of the ZnO is preferably at least about 90 m²/g, e.g. about 90 to 110 m²/g. The zinc oxide may be present in the detergent composition in an amount, for example, of about 0.1 to 5.0 wt. %, preferably about 0.5 to 1.5 wt. %, based on the weight of the total composition.

Because of its small particle size and to avoid excessive dusting and reduction in surface area when contacted with air containing water vapor and $CO_2$, the zinc oxide is advantageously stored and added to the composition in the form of a dispersion in an organic liquid which has no adverse effect on the action of the detergent, e.g., $C_{10}$/$C_{12}$/$C_{14}$ fatty acid such as coconut fatty acid, triglyceride, octyl palmitate, etc. If the organic liquid is solid at room temperature, it may be liquified by heating in the preparation of the dispersion.

To enhance its deodorization effect, the detergent composition of this invention preferably also contains sodium bicarbonate (SBC). The SBC may have an average particle size within the range, for example, of about 10 to 700 microns, preferably about 10 to 400 microns and may be present in an amount, for example, of about 1 to 15 wt. %, preferably about 7 to 12 wt. % based on the weight of the total composition. In the production of a toilet soap or detergent composition under the invention which is solid at room temperature, the use of SBC having an average particle size near the lower end of the foregoing range, e.g., about 10 to 25 microns, is especially beneficial since it results in a particularly smooth-textured product.

The presence of both small particle size ZnO and SBC in a detergent composition is believed to cause a synergistic effect on the deodorant properties of the composition.

The detergent composition of this invention may also contain varying quantities of compatible adjuvants which do not materially interfere with the bactericidal effect of the small particle size ZnO and the direct deodorizing effect of the SBC, if present. Typical of such compatible adjuvants are fillers and pigments such as titanium dioxide, diatomaceous earth, any of various colored pigments, dyes, fragrances, optical brighteners and bactericidal and bateristatic compounds other than zinc oxide such as cetylpyridinium chloride.

The composition may be in solid form such as bars, flakes, chips, or powders or in liquid form. In addition to the possible differences discussed previously in the chemical nature of the active fatty acid salt in solid and liquid soap compositions, solid detergent compositions often contain a significant amount of pigment and filler and little or no water while liquid compositions generally contain no pigment or filler but may contain a significant amount of water in which the active soap or synthetic detergent component is soluble.

The small particle size zinc oxide and SBC, if used, may be added to the detergent composition at any point in the conventional manufacture of these products. For example in the production of solid soap bars under the invention, soap chips may be weighed into a mixer, the contemplated compatible adjuvants, if any, added thereto, and the total mixed for a long enough period to achieve uniformity of the mix. The zinc oxide and SBC, if used, may then be added to the mixer and the mixing continued until these ingredients are uniformly dispersed in the mixture. After mixing, the composition can be formed into framed or milled soap bars in accordance with the general procedure of the soap making art.

The following examples further illustrate the invention.

Examples 1–3

Chips of a solid, commercially available soap, e.g., a mixture of sodium salts of about 80 wt. % tallow and about 20 wt. % of coconut oil and/or palm kernel oil fatty acids, were masticated in a mixing machine at a temperature of about 25° C. until a uniform appearing plastic mass was obtained. Varying amounts of zinc oxide having a particle size in the range of about 0.01 to 5 microns as a dispersion in coconut fatty acid, and SBC having a particle size in the range of about 20 to 700 microns were gradually added to the soap samples in the mixer and mixing was continued until the soap samples appeared completely homogeneous, i.e., for a period of about 30 minutes. The soap samples were then formed into frame or milled soap bars using known techniques.

The amounts of zinc oxide and SBC present in the examples are shown in the following table.

TABLE

| Example | Zinc Oxide, wt. % | SBC, wt. % |
|---|---|---|
| 1 | 0.1 | 9.9 |
| 2 | 0.5 | 9.5 |

TABLE-continued

| Example | Zinc Oxide, wt. % | SBC, wt. % |
| --- | --- | --- |
| 3 | 1.0 | 9.0 |

The soaps of the foregoing examples exert a larger deodorizing effect when used in ordinary washing operation than the same soaps containing no zinc oxide or SBC.

I claim:

1. A toilet deodorant detergent composition comprising a surfactant, and as deodorizing components, about 0.1 to 5.0 wt. % of zinc oxide having an average particle size no greater than about 10 microns and a surface area of at least about 90 $m^2/g$, and about 1 to 9.9 wt. % of sodium bicarbonate, based on the total composition.

2. The composition of claim 1 wherein said surfactant is a soap.

3. The composition of claim 2 in the form of a solid bar.

4. The composition of claim 1 wherein said surfactant is a synthetic detergent.

5. The composition of claim 1 wherein said zinc oxide has a particle size in the range of about 0.01 to 5 microns.

6. The composition of claim 5 wherein said particle size of zinc oxide is in the range of about 0.01 to 0.1 microns.

7. The composition of claim 6 wherein said amount of zinc oxide is about 0.5 to 1.5 wt. %.

8. The composition of claim 1 wherein said sodium bicarbonate (SBC) has an average particle size in the range of about 10 to 700 microns.

9. The composition of claim 8 wherein said particle size of sodium bicarbonate (SBC) is in the range of about 10 to 400 microns.

10. The composition of claim 9 wherein said composition is solid at room temperature and said particle size of sodium bicarbonate (SBC) is in the range of about 10 to 25 microns.

11. The composition of claim 8 wherein said SBC is present in an amount of about 7 to 12 wt. % based on the total composition.

12. A method for preparing the composition of claim 1 wherein said zinc oxide is mixed with said surfactant as a dispersion in an organic liquid.

13. The method of claim 12 wherein said organic liquid is coconut fatty acid.

14. A method comprising washing the human body with the composition of claim 1.

15. The composition of claim 1 wherein said surface area is about 90 to 110 $m^2/g$.

16. The composition of claim 1 in the form of a solid personal toilet bar.

* * * * *